United States Patent
Hanna

(10) Patent No.: US 8,074,659 B2
(45) Date of Patent: Dec. 13, 2011

(54) METHOD AND APPARATUS FOR PROTECTING TEETH, PREVENTING THE EFFECTS OF BRUXISM AND PROTECTING ORAL STRUCTURES FROM SPORTS INJURIES

(76) Inventor: Wadia M. Hanna, Albany, NY (US)

( * ) Notice: Subject to any disclaimer, the term of this patent is extended or adjusted under 35 U.S.C. 154(b) by 286 days.

(21) Appl. No.: 12/462,724

(22) Filed: Aug. 7, 2009

(65) Prior Publication Data

US 2011/0030704 A1    Feb. 10, 2011

(51) Int. Cl.
*A61C 5/14*    (2006.01)
*A61C 3/00*    (2006.01)
(52) U.S. Cl. ............................................. 128/861; 433/6
(58) Field of Classification Search .................. 128/846, 128/857, 859, 861, 862, 848; 433/2, 6, 18, 433/20, 21, 22
See application file for complete search history.

(56) References Cited

U.S. PATENT DOCUMENTS

| | | | | |
|---|---|---|---|---|
| 4,955,393 A * | 9/1990 | Adell | | 128/859 |
| 6,247,926 B1 * | 6/2001 | Thornton | | 433/48 |
| 6,374,824 B1 * | 4/2002 | Thornton | | 128/201.26 |
| 2002/0142258 A1 * | 10/2002 | Chishti et al. | | 433/6 |

* cited by examiner

*Primary Examiner* — Patricia Bianco
*Assistant Examiner* — Tarla Patel
(74) *Attorney, Agent, or Firm* — Robert K. Tendler

(57) ABSTRACT

A comfortable multiple layer mouth protector is provided for strength and ease of fit to minimize if not completely and gradually eliminate bruxism, with spring biasing keeping the maxillary and mandibular mouth protector arches in place and apart, eliminating snoring and permitting easy breathing. In addition, this Mouth protector protects oral structures from sports injuries.

16 Claims, 6 Drawing Sheets

Stock mouth guard

Boil and bite mouth guard

METHOD AND APPARATUS FOR PROTECTING TEETH, PREVENTING THE EFFECTS OF BRUXISM AND PROTECTING ORAL STRUCTURES FROM SPORTS INJURIES

FIELD OF THE INVENTION

This invention relates to mouth protectors and more particularly to an easily fitted mouth protector having a multi-layer metal reinforced structure for prevention of athletic and other injuries, with the mouth protector being springs loaded to provide a minimally invasive system that allows limited movement of teeth relative to each other, yet keeps the teeth apart, thus to control bruxism, snoring, and allows breathing.

BACKGROUND OF THE INVENTION

There are numerous mouth guard protectors which typically cover the upper teeth and can cushion a blow to the face, minimizing the risk of broken teeth and injuries to the soft tissues of the mouth.

In addition to such mouth protectors, there are numerous mouth guards on the market created to protect children and adults teeth from the effects of bruxism. Whether the mouth guard is to prevent the effects of bruxism or are created to protect athletes, sports participants and others from injuries inflicted on the face, jaws, teeth and soft tissues, such prior art mouth guard protectors which being inexpensive and come preformed, ready to wear don't fit very well. Moreover, they are bulky and can make breathing and talking difficult. Additionally, mouth protectors utilized in the sports arena are not particularly well adapted to prevent the effects of bruxism.

As part of the prior art are so-called boil and bite mouth guards which are mouth protectors available from many sporting goods stores and offer a better fit than standard stock mouth protectors. Typically they are softened in water, whether heated or not, and are inserted and allowed to adapt to the shape of the individual's mouth. However, if directions are not followed carefully, the patient can end up with a poor fitting mouth protector.

Further, there are custom fitted mouth protectors made up by a dentist for an individual patient. Note, they are more expensive than the versions described above, but because they are customized they can offer a better fit than anything bought off-the-shelf. These mouth protectors come in two categories, mainly a vacuum custom made mouth guard and a pressure laminated custom made mouth guard.

The above mouth protectors are primarily used to ward off impact and are not particularly well adapted to eliminating the effects of grinding of one's teeth.

As to bruxism, there is a prior art teeth grinding protector available on the market called an NTI-TSS Grinding Protector in which a small splint is placed on the anterior teeth to keep the back teeth apart. These protectors are only partially successful and not often used. Note if the protector is loose and falls, there is a danger of being swallowed accidentally.

As will be appreciated, with all of the above mouth guards, there are many complaints from patients regarding the mouth protector fitting well in their mouths and children will rarely ever wear them due to the ill fitting nature of the mouth guard as well as other inconveniences in their use.

Note for the present purposes, bruxism is a habit of clenching and grinding of the teeth. It most often occurs at night during sleep, but may also occur during the day. It is an unconscious behavior or habit perhaps performed to release anxiety, aggression or anger. Bruxism occurs when people clench or tightly hold their top and bottom teeth together or grind their teeth, meaning sliding the teeth back and forth over each other. This wears away the teeth surfaces, with teeth surface abrasion the most clinically important sign of bruxism. Note, as far as pediatric bruxism is concerned, there is a standard type of bruxism or a so-called eccentric bruxism, both of which are preventable with the proper type of fitted mouth protector.

By way of further background, U.S. Pat. Nos. 5,823,193; 5,876,199; 5,678,993; 5,636,397; 5,499,633; 5,163,840; and 5,130,838 are examples of various types of mouth guards.

Their uses included prevention against injury, prevention of snoring, providing a jaw joint protective device, and include soft denture liner materials. Moreover, some of the above patents are useful in orthodontic correction procedures and protect teeth from bruxism.

More particularly, there has been an observation that during practicing and tending to dental treatment for pediatric patients, it is well documented that over 30% of children have a bruxism or grinding problem. As a result teeth are considerably worn and the resulting wear causes pulp exposure most of the time. As well as being observed in children the above applies to the adult population.

In summary, many complaints are heard from patients about the inability to wear a mouth protector for one reason or another. Moreover, even when tight fit mouth protectors are made of hard plastic material which reduces the acceleration of occlusional wear, they do not eliminate the problem.

SUMMARY OF INVENTION

In order to provide an easily fit strong mouth protector, a multi-layer structure is used in a two piece mouth protector including maxillary and mandibular arches held together by spring assemblies exerting a very light spring force. The multi-layer metal mesh reinforced structure protects the teeth against abrasion by providing tough opposed surfaces to take the wear while cushioning the teeth. Moreover, the metal mesh layer malleability helps shape and conform the mouth Protector to each individual patient's dental arches.

It will be appreciated that that the spring tension of the spring assembly is light and can not be such as to cause pain or disturbance of any sort. Moreover, the spring tension is set well below that which would result in temporal mandibular joint (TMJ) muscles pain but is high enough to provide stability and retention to the mouth protector.

In one embodiment, the multi-layer reinforced structure provides exceptional protection against not only bruxism but also tough sports injuries in that it dissipates the forces applied on the face, jaws and soft tissues to prevent tooth, gum and jaw damage such as jaw bone fracture.

Note that the spring structure is used to keep the teeth apart especially during sleep periods, with the multi-layer mouth protector opposing the high occlusal forces that for children 8 to 10 years of age averages between 126.15 and 239 Newtons. As will be appreciated, the average bite force for adults ranges between 380-728 Newtons (84.4-160.6 pounds).

In addition to the multi-layer structure that provides a better fit and better protection against occlusal forces, in order to minimize noticing the spring, in one embodiment a lost motion spring device is used between the maxillary area and mandibular arches. The lost motion device while keeping the teeth apart and in place over the teeth permits limited arch movement to accommodate slight movements of the mouth. The lost motion spring apparatus thus permits only limited anterior, posterior and lateral movements by exerting virtually undetectable amounts of pressure, and this only after the arches have moved by a limited amount. It has been found that this minute pressure is in fact capable of limiting the motion that produces grinding. The role of the springs in the mouth protector is to allow movement in protrusion or retrusion and in lateral directions on the order of 10 to 15 millimeters, while exerting little or non-obtrusive pressure or force to keep the maxillary and mandibular arches apart and in place.

As to the multi-layer structure employed in the subject invention, in one embodiment there is a tough outer layer of silicone and rubber. Sandwiched in this outer layer is a tough but malleable metal mesh reinforcing layer embedded in the silicone layer. Next to the composite sandwich of the tough silicone layer and malleable metal layer is a gel layer on top of which a soft cushiony and tear resistant soft silicone layer is positioned which molds to the teeth to provide an exceptional, comfortable fit without having to customize the mouth protector.

In one embodiment, total thickness of the tough outer layer of heavy silicone is on the order of 5 to 6 millimeters, with this thickness also including the metal mesh embedded therein. The gel layer is compressible to a depth of 3 to 4 millimeters, whereas the stretchable silicone soft and compressive layer is on the order of 4 to 5 millimeters.

The stretchable silicone soft and compressive layer has a modest amount of memory that provides a tooth imprint when it conforms around the teeth.

However regardless of whether the stretchable silicone soft and compressive layer has memory, when placing the mouth protector over the teeth and pressing down, the result is a comfortable mouth protector which because of its multi-part construction provides exceptional protection against tooth damage, especially in athletic activities. Additionally, because of the embedded metal mesh and the tough heavy silicone outer layer, grinding damage to the teeth is virtually non-existent.

Moreover, because of the lost motion spring structure which permits relatively small protrusion/retrusion and lateral movement, teeth grinding is also kept to minimum while at the same time providing a device which is virtually undetectable in terms of the spring tension of the springs involved. This permits undisturbed sleep for individuals who grind their teeth.

Also, because the spring structure keeps the mouth protector separated, the subject device can also be utilized to combat snoring.

As an added advantage the subject mouth protector teaches pediatric patients and others gradually not to grind their teeth. Training with the subject mouth protectors has resulted in greatly diminished teeth grinding when used over an extended period of time. It has therefore been found that bruxism can be treated through a learning process using the subject device.

In summary, a comfortable multiple layer mouth protector is provided for strength and ease of fit to minimize if not completely eliminate bruxism, with spring biasing keeping the maxillary and mandibular mouth protector arches in place and apart, eliminating snoring and permitting easy breathing.

BRIEF DESCRIPTION OF THE DRAWINGS

These and other features of the subject invention will be better understood in connection with the Detailed Description, in conjunction with the Drawings, of which.

DETAILED DESCRIPTION

Figure 1:
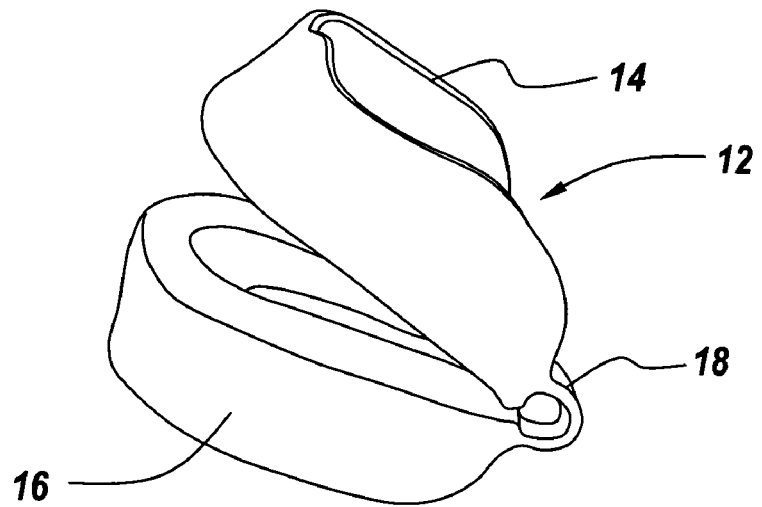
FIG. 1 is a diagrammatic illustration of a stock mouth guard prevalent in the prior art.

Referring now to FIG. 1, a standard stock mouth guard 12 includes arches 14 and 16 hingedly attached using an integral hinge 18. These stock mouth guards do not fit the mouth properly as they are ready-made for the market. The result is that their use is limited because of the discomfort involved as well as the weight and bulk of the devices which makes their use sporadic, especially when these devices are used to prevent bruxism in children.

Figure 2:
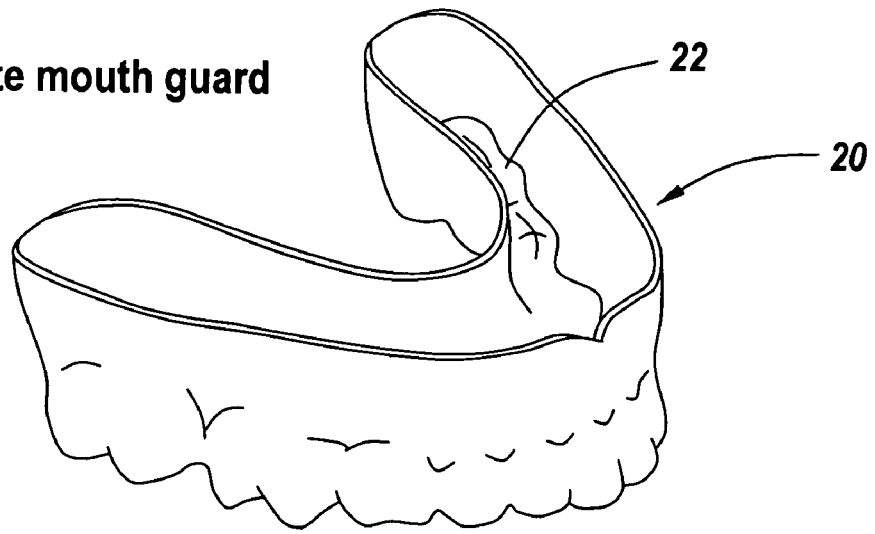
FIG. 2 is a diagrammatic illustration of a boil and bite prior art mouth guard in which the material is immersed in hot water at which point the individual bites on the mouth guard to deform the guard to provide for a close fit.

Referring to FIG. 2, an upper arch mouth guard 20 is a so-called boil and bite mouth guard which is not generally designed to combat grinding of teeth. Rather it is used to protect athletes from mouth and tooth damage in which the mouth guard is conformed to the teeth by first heating it as by boiling it in water and then having the individual clamp down on the mouth guard such that its interior layer 22 conforms to the teeth, and upon cooling retains the shape of the teeth. These mouth guards however do not provide for a perfect fit and in general are only used to protect the upper teeth. Because of the material of which they are made, if attempts are made to use them for preventing the effects of bruxism, their materials are too soft because grinding itself wears through the mouth protector.

Figure 3:
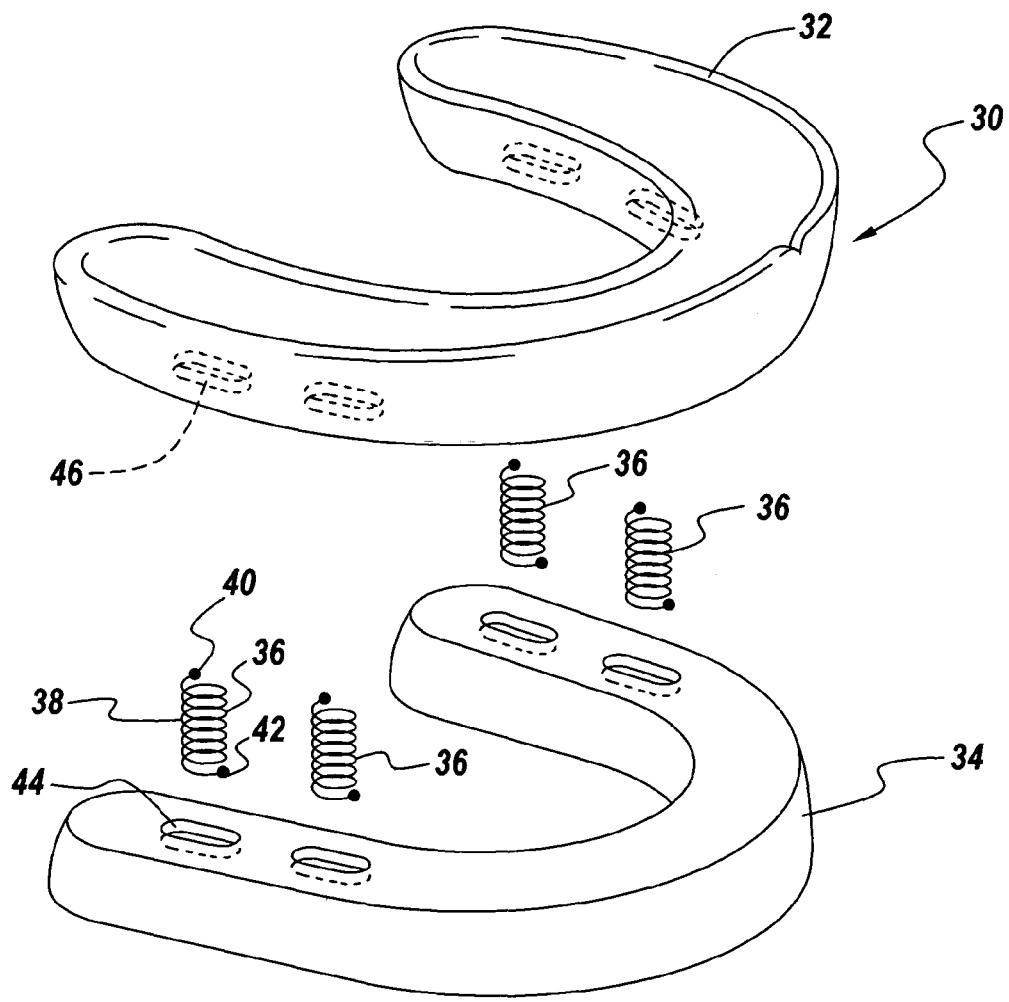
FIG. 3 is an exploded view of the subject mouth protector showing the maxillary and mandibular arches interconnected with a spring assembly or structure that separates the two arches and keeps them in place in which the spring assembly includes springs having ends retained in slots to provide lost motion devices for limited protrusion and retrusion.

Referring now to FIG. 3, in an exploded view the subject mouth protector 30 includes an upper or maxillary arch 32 and a mandibular arch 34 which are held in position relative to each other. In one embodiment spring assemblies 36 keep the arches aligned and allow relative movement while at the same time keeping the arches and therefore the teeth apart.

The spring assemblies include springs 38 having ends or buttons 40 and 42 which are retained in opposed slots 44 and 46. The button or end structure sliding in slots 44 and 46 result in a lost motion device which provides in part for the limited protrusion/retrusion operation of the subject mouth piece. The action of the lost motion device in allowing protrusion/retrusion only comes into play when a button end reaches the end of its respective slot. Thus the lost motion permits limited arch movement.

The use of the subject spring structure is important because it promotes the use of the mouth guard, especially for children who are disinclined to use such structures in their mouth because of discomfort. If one attempts to insert a rigid structure into a child's mouth the discomfort can be both painful and a distraction during sleep, since grinding (bruxing) tends to work during sleep.

If the mouth protector is not used, then its whole purpose or reason for being is eliminated. The subject spring structure which anchors the upper and lower arches relative to one another is almost unfelt when the mouth protector is in place while still serving the function of keeping the arches 32 and 34 separated as illustrated by double-ended arrow 46.

This separation, it will be appreciated, not only tends to eliminate the problem of teeth grinding but also by keeping the mouth open and creates an air passage for ease of breathing during sleeping. Because the air passage is open, the subject device in addition to eliminating the effects of bruxism, also to a large extent eliminates snoring.

Note that occlusal force can be large and can overcome the spring assembly's ability to keep the arches separated. However, the effects of bruxism are eliminated due to the strong multi-layer, metal-reinforced arches when the arches touch. Moreover, the spring assemblies limit protrusion and retrusion to minimize any grinding that does occur.

Figure 4:
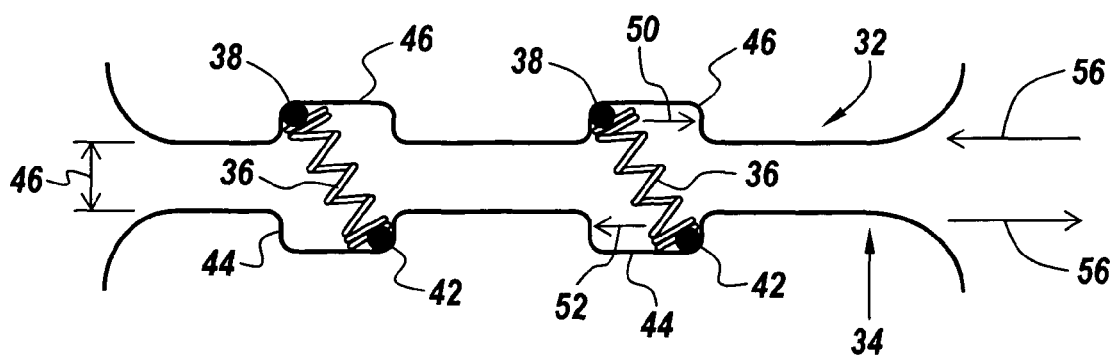
FIG. 4 is a diagrammatic illustration of the lost motion spring assemblies of FIG. 3 showing the separation of the arches as well as the ability to permit limited protrusion and retrusion of the arches of the subject invention.

In FIG. 4 it can be seen that the button ends 38 and 42 move in the directions illustrated by arrows 50 and 52 in respective slots 44 and 46, with the protrusion or retrusion illustrated by arrows 54 and 56.

It has been found that the lost motion afforded by the movement of the buttons in their slots as well as the spring constants of the springs permits only limited lateral arch movement on the order of 4 to 15 millimeters.

Because the arches are not locked together limited movement of the jaw and teeth during sleep is accommodated without being obtrusive enough to waken the individual or result in discomfort.

Figure 5:
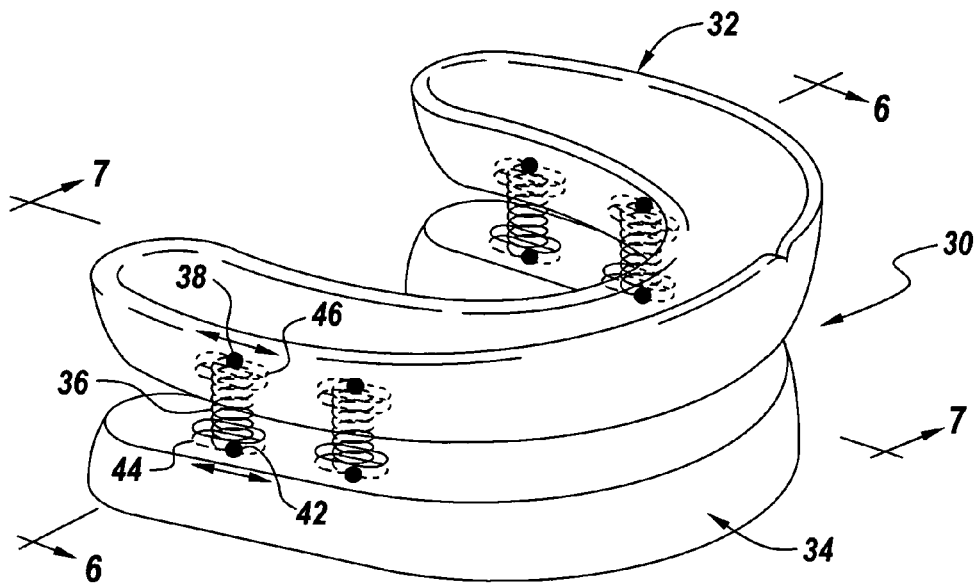
FIG. 5 is a diagrammatic illustration of the mouth protector of FIG. 3 showing the arches in an unexploded view, with the arches mounted one to the other utilizing the spring assemblies of FIGS. 3 and 4.

Referring to FIG. 5, mouth protector 30 is shown in its assembled position with arch 32 held in place above arch 34 as illustrated. Also shown are springs 38 having ends 40 and 42 in respective slots 44 and 46.

Figure 6:
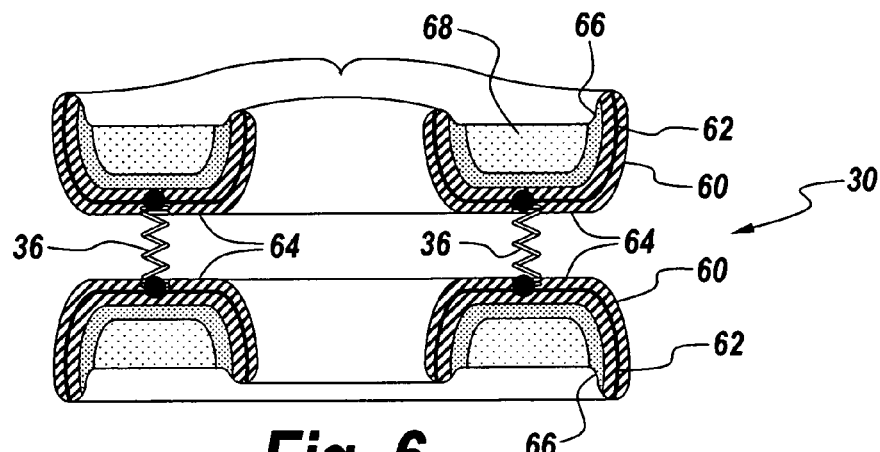
FIG. 6 is a cross sectional view of the mouth protector of FIG. 5 illustrating the multi-layer structure of each of the arches in which the outer layer is of a tough silicone construction with a metal mesh layer embedded therein, on top of which is a dense liquid gel layer followed by a soft cushiony malleable silicone layer which is deformable around the teeth that provide an imprint therein.

Referring to FIG. 6, what is shown is a cross section of mouth protector 30 along lines 6-6.

Here the multi-layer structure of the subject mouth protector can be seen to include a tough outer layer 60 which in one embodiment is either a silicone layer, a rubber layer or both which has occlusal slots about 10 millimeters in size that function to retain spring assembly 36 in a sliding fit.

Embedded in outer layer 60 is a metal mesh layer 62 which is a tough but malleable layer that is embedded in the silicone layer. This metal mesh layer absorbs the applied occlusal forces which are in general perpendicular to the surface 64 of outer layer 60.

Going towards the interior of the mouth protector, a gel layer 66 is used as an intermediate energy absorbing cushioning layer between the outer layer and a soft cushiony deformable inner layer 68 made of soft cushiony and tear resistant material.

In one embodiment, this material has a memory such that when the mouth protector is in place and the individual clamps down on the mouth protector an imprint of the teeth is left in the soft cushiony and tear resistant layer to provide for exceptional fit, and therefore exceptional comfort.

Soft cushiony layer 66 is of the consistency of silly putty which has a memory that maintains the tooth imprint once the mouth protector is first used.

Figure 7:
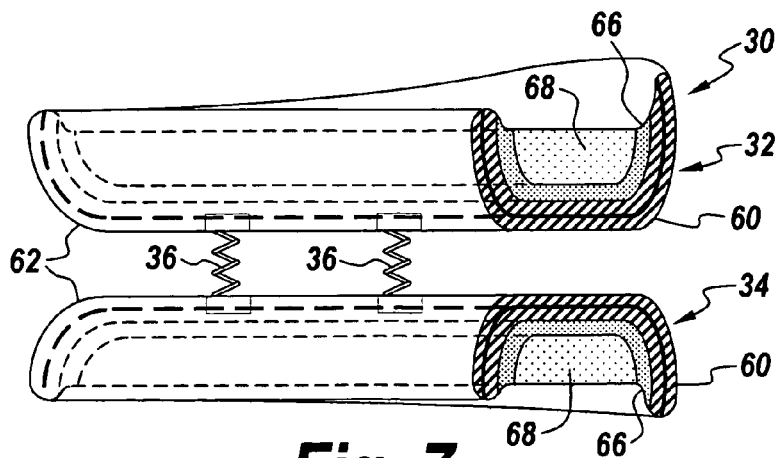
FIG. 7 is a diagrammatic and cross sectional view of the mouth protector of FIG. 5 showing the layers of FIG. 6, illustrating the metal screen layer in dotted outline.

Referring to FIG. 7, this drawing is a cross section of mouth protector 30 of FIG. 5 taken along lines 7-7. Here, like elements of the mouth protector carry like reference characters. It can be seen that the metal mesh layer 62 runs the length of the arch as do the remainder of the layers of the mouth protector.

Figure 8:
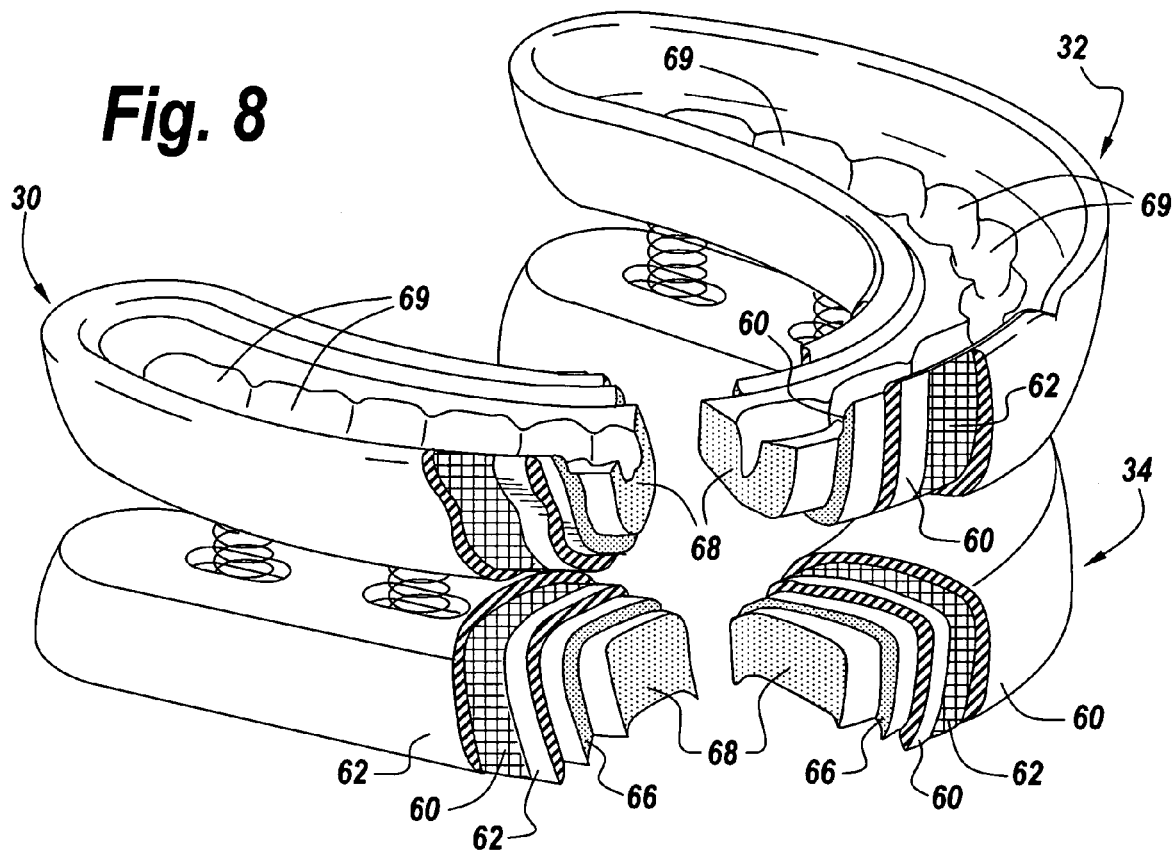
FIG. 8 is a perspective view of the mouth protector of FIG. 5 with the layers of the mouth protector shown in cutaway.

Referring now to FIG. 8 as can be seen in greater detail, mouth protector 30 is shown in cutaway to expose the various layers. Here it can be seen that inner layer 68 rests upon gel layer 66 which in turn rests upon outer layer 60, with the metallic mesh layer 62 embedded in the outer layer. Note that in FIG. 8 the inner layer 68 can be provided with prefabricated teeth imprints 69 that cushion and surround the teeth, with extra thickness of layer 68 being provided beneath the teeth to protect the teeth from impact.

Figure 9:
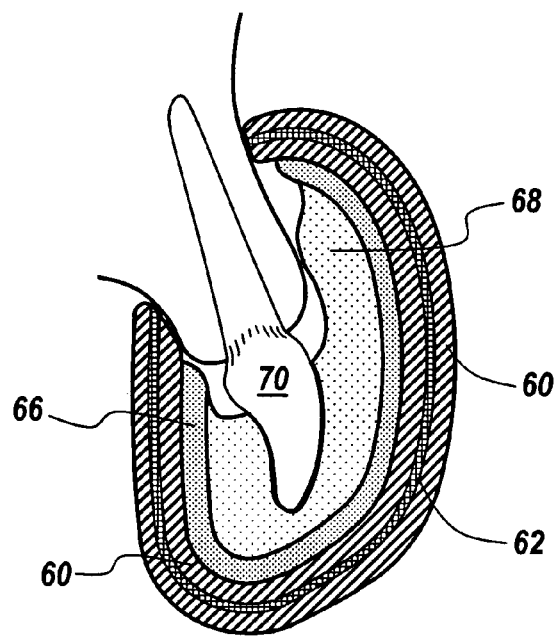
FIG. 9 is a diagrammatic illustration in partial cross section showing the projection of a tooth into the soft inner layer of the mouth protector.

Referring to FIG. 9, the cushioning of tooth 70 is shown in that the tooth is surrounded by inner soft silicone layer 68, with the gel layer 66 being on the order of 3 to 4 millimeters in thickness. The heavy silicone outer layer 60 is on the order of 5 to 6 millimeters in thickness that includes the thickness of the embedded metal mesh layer.

Finally, it will be noted that the stretchable silicone soft and compressive layer which surrounds the tooth, in one embodiment is on the order of 4 to 5 millimeters in thickness, at least from the bottom of the tooth to the interface between the inner layer and the gel layer.

Figure 10:
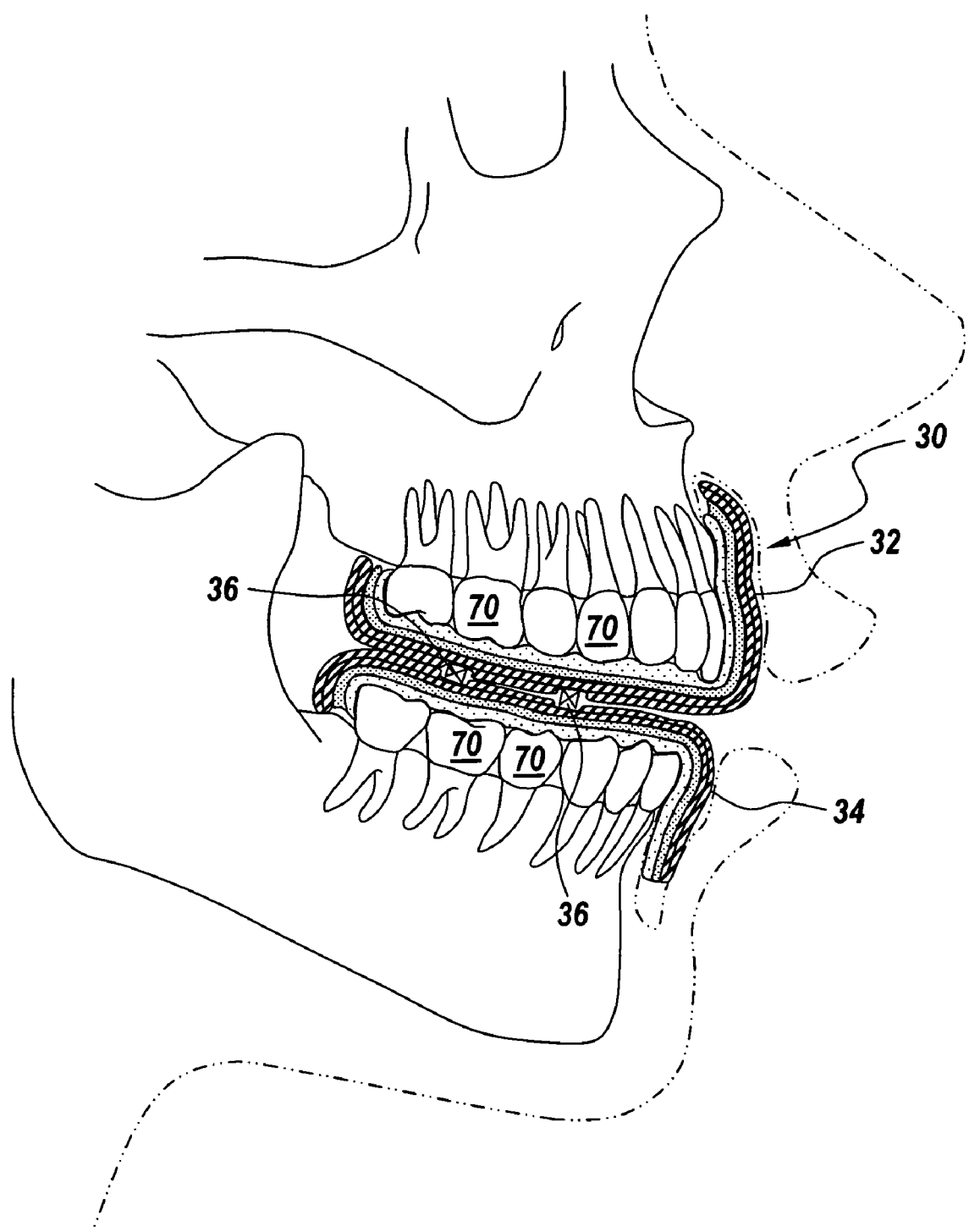
FIG. 10 is a diagrammatic illustration of the mouth protector in place showing the limited movement allowance due to the spring assemblies, also showing the protection of the teeth when using the multi-layer device.

FIG. 10 is a diagrammatic illustration of the mouth protector 30 in use showing teeth 70 in the maxillary and mandibular arches in which lost motion spring assemblies 36 permit a 4 to 15 millimeter movement allowance when the mouth protector is in place.

As can be seen, the clenching of the teeth results in the contacting of arches 32 and 34 to the extent that the spring tension of spring assembly 36 is overcome.

However, even when the arches 32 and 34 touch, the relative movement between the arches is limited which eliminates the debraiding that normally occurs during bruxism. Note that arches 32 and 34 in general conform to the Curve of Spee, as illustrated.

Figure 11:
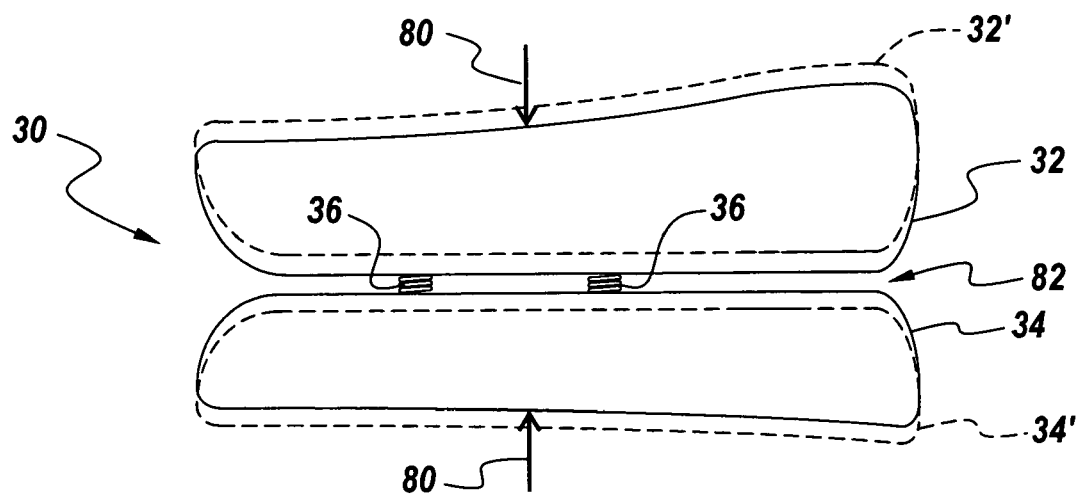
FIG. 11 is a diagrammatic illustration showing the limiting of the space between the arches of the subject mouth protector so as to provide a space therebetween for eliminating the effects of bruxism as well as providing for snoring protection and to facilitate a clear airway through the mouth; and, FIG. 12 is a diagrammatic illustration of limited protrusion/retrusion movement due to lost motion devices provided by the spring assemblies that anchor the arches together.

More particularly and referring to FIG. 11, arches 32 and 34 are shown with springs 38 compressed in response to compressive forces shown by arrows 80 such that when in use the arches move from their dotted positions 32' and 34' to the positions shown. The spring constant of the spring structure limits the movement of the arches as they move together, thus to provide spacing 82 to provide an air passage. Note, the occlusive forces applied to the mouth protector overcome the spring tension and result in the arches touching each other.

Figure 12:
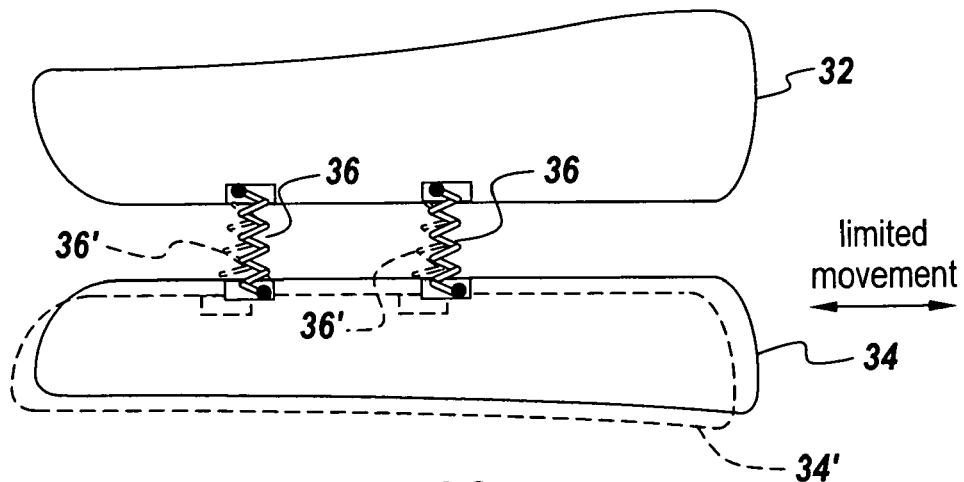

To prevent grinding of the arches themselves and as can be seen from FIG. 12, spring assemblies 36 move as illustrated from the dotted position 36' to the position 36 which allows lower arch 34 to move from its original position to position 34' relative to arch 32.

It is the purpose of the subject invention to provide a multi-layer structure which is exceedingly tough to protect the teeth while at the same time providing an exceptionally good fit without having to be customized to the individual. Moreover, the ability to keep the arches separated utilizing the subject spring structure to a certain extent eliminates the effects of bruxism, while at the same time providing an open airway during sleep as well as preventing snoring.

The multi-layer structure provided by the subject mouth protector provides exceptional protection for the teeth, not only against the grinding action associated with bruxism, but also against physical sports injuries.

The maxillary and mandibular mouth protector parts, as an option, can be connected in the posterior parts by a hinge to facilitate stability and articulation of the upper and lower parts. Note in this embodiment, tension springs are not used.

However with the spring structure and more especially with the lost motion spring assemblies, it is possible to encourage pediatric use of the device because of the ease of fit and unobtrusiveness. Moreover, use of the subject mouthpiece has been found to have a teaching component in which children are gradually taught to stop grinding their teeth.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. Apparatus for protecting teeth and preventing the effects of bruxism comprising:
    a mouth protector including a maxillary arch and mandibular arch, each of said arches having a multi-layer structure including a wire reinforced outer layer and a soft, malleable and deformable inner layer, the reinforcing of said arches absorbing energy imparted to said arches and a spring biasing assembly positioned between said arches to provide space between said arches, said spring biasing assembly including spring members having a light spring tension such that the use of said mouth protector is not only comfortable but one in which the use of the spring biasing assembly is virtually undetectable, said spring biasing assembly including spring members having ends and wherein said arches have end receiving slots therein for receiving respective ends of said spring members such as to provide said spring biasing assembly with a lost motion function, thereby to permit only limited protrusion/retrusion of said arches relative one to the other, whereby bruxism is reduced due to the limited relative movement of said arches.

2. The apparatus of claim 1, wherein said soft, malleable and deformable upper layer includes teeth imprints that cushion and surround the teeth with extra thickness beneath the teeth in order to protect the teeth from force impacts.

3. The apparatus of claim 1, wherein the wire reinforced outer layer includes a malleable metal mesh layer.

4. The apparatus of claim 3, wherein said metal mesh layer is embedded in said outer layer.

5. The apparatus of claim 1, and further including a gel layer interposed between said inner and outer layers to provide an intermediate energy absorbing and cushioning layer therebetween.

6. The apparatus of claim 1, wherein said outer layer includes a tough silicone layer.

7. The apparatus of claim 1, wherein said inner layer is a soft cushiony layer of tear resistant material.

8. A method for protecting teeth from sports injury and the effects of bruxism, comprising:
    providing a multi-layer mouth protector including opposed maxillary and mandibular arches, each of the arches having a tough outer layer and a soft deformable but tear resistant inner layer, the inner layer having prefabricated teeth imprints to fit and surround the teeth when the mouth guard is in place and a spring biasing assembly positioned between said arches to provide space between said arches, said spring biasing assembly including spring members having a light spring tension such that the use of said mouth protector is not only comfortable but one in which the use of the spring biasing assembly is virtually undetectable, said spring biasing assembly including spring members having ends and wherein said arches have end receiving slots therein for receiving respective ends of said spring members such as to provide said spring biasing assembly with a lost motion function, thereby to permit only limited protrusion/retrusion of said arches relative one to the other, whereby bruxism is reduced due to the limited relative movement of said arches; and,
    using the mouth guard to protect an individual's teeth, whereby the mouth guard is both strong and abrasion resistant while at the same time being both comfortable and self adapted to fit the mouth of the individual due to the deformable inner layers of the arches.

9. The method of claim 8, wherein the mouth guard is inserted into the individual's mouth prior to sleep for protecting the individual's teeth against grinding abrasions due to bruxism.

10. The method of claim 8, wherein the arches are reinforced utilizing a metal mesh layer in the outer layers of the arches.

11. The method of claim 8, and further including providing a spring biasing assembly between the arches to position the arches relative to each other and for initially holding the arches apart, thereby to provide an airway during sleep and to prevent snoring.

12. The method of claim 11, and further including the step of limiting the protrusion/retrusion movement of the arches utilizing the spring biasing assembly, whereby only limited grinding motion between the arches is permitted during sleep.

13. The method of claim 12, wherein the limiting of the protrusion/retrusion movement is accomplished using lost motion devices between the arches with the lost motion devices permitting arch movement until such time as motion of the lost motion devices has reached the limit thereof.

14. A wearable, comfortable mouth protector for use with pediatric patients to correct bruxism, comprising:
    a mouth protector having a pair of opposed arches adapted to be positioned adjacent the maxillary and mandibular features of the patient's mouth in which the arches contain a deformable, soft, compliant material adapted to surround the teeth of the patient, said soft, compliant material having prefabricated teeth imprints to provide comfort and cushion for the teeth upon receiving inner or outer force impacts, and to deform with a memory to provide a teeth imprint after use such that the arches comfortably fit the patient from one use to the next, a spring biasing assembly positioned between said arches to provide space between said arches, said spring biasing assembly including spring members having a light spring tension such that the use of said mouth protector is not only comfortable but one in which the use of the spring biasing assembly is virtually undetectable, said spring biasing assembly including spring members having ends and said arches having end receiving slots therein for receiving respective ends of said spring members such as to provide said spring biasing assembly with a lost motion function, thereby to permit only limited protrusion/retrusion of said arches relative one to the other, whereby bruxism is reduced due to the limited relative movement of said arches and whereby pediatric use is encouraged due to the comfort and non-obtrusiveness of the mouth protector.

15. The apparatus of claim 14, wherein said arches include multiple layers including said soft deformable layer and an outer layer of tough wear-resistant material, with said arches protecting pediatric patient's teeth against erosion or grinding due to bruxism.

16. A method for teaching patients to avoid bruxism, comprising the step of:

providing a mouthpiece having maxillary and mandibular arches maintained in spaced relationship to be inserted into the patient's mouth and providing spring assemblies between the arches to promote the spacing of the arches and to limit arch movement, said spring biasing assemblies positioned between said arches to provide space between said arches, said spring biasing assembly including spring members having a light spring tension such that the use of said mouth protector is not only comfortable but one in which the use of the spring biasing assembly is virtually undetectable, said spring biasing assembly including spring members having ends, said arches having end receiving slots therein for receiving respective ends of said spring members such as to provide said spring biasing assemblies with a lost motion function, thereby to permit only limited protrusion/retrusion of said arches relative one to the other, whereby wearing the mouthpiece gradually teaches the patient to stop teeth grinding.

* * * * *